United States Patent [19]

Ward

[11] Patent Number: 4,526,967
[45] Date of Patent: Jul. 2, 1985

[54] BENZOQUINOLIZINES AND USE AS α2-ADRENOCEPTOR ANTAGONISTICS

[75] Inventor: Terence J. Ward, Slough, England

[73] Assignee: John Wyeth & Brother Limited, Maidenhead, England

[21] Appl. No.: 590,653

[22] Filed: Mar. 19, 1984

[30] Foreign Application Priority Data

Mar. 25, 1983 [GB] United Kingdom ............... 8308321
Dec. 13, 1983 [GB] United Kingdom ............... 8333232

[51] Int. Cl.³ .................. A01N 43/40; A61K 31/435; C07D 455/06; C07D 221/06
[52] U.S. Cl. .................................................... 546/95
[58] Field of Search ................. 546/95, 109; 424/256

[56] References Cited

U.S. PATENT DOCUMENTS 4,076,820 2/1978 Archibald et al. ............... 546/95
4,154,139 6/1984 Ward et al. ...................... 546/95

FOREIGN PATENT DOCUMENTS 2083029 3/1982 United Kingdom ............... 471/4
2106909 4/1983 United Kingdom ............... 424/256

OTHER PUBLICATIONS

Archibald, et al., *J. Med. Chem.* 1983, (26)(3), 416–420.

*Primary Examiner*—Henry R. Jiles
*Assistant Examiner*—Ann Bucci
*Attorney, Agent, or Firm*—George Tarnowski

[57] ABSTRACT

The invention concerns benzoquinolizines of general formula

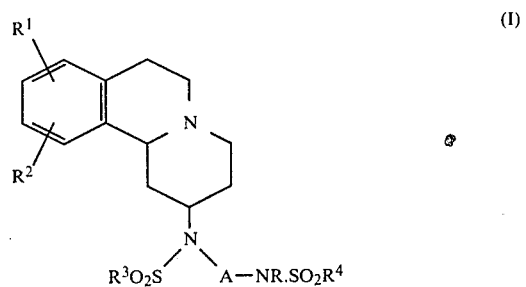

and their pharmaceutically acceptable acid addition salts. In formula (I), R represents hydrogen or lower alkyl, $R^1$ and $R^2$ which may be the same or different each represent hydrogen, lower alkyl, lower alkoxy or halogen, $R^3$ and $R^4$ which may be the same or different each represents lower alkyl, halo(lower)alkyl or aryl and A represents a lower alkylene group having 1 to 3 carbon atoms in the chain between the two N atoms. The compounds possess α2-adrenoceptor antagonistic activity in warm blooded animals.

10 Claims, No Drawings

BENZOQUINOLIZINES AND USE AS α₂-ADRENOCEPTOR ANTAGONISTICS

The invention relates to benzoquinolizines, to processes for preparing the benzoquinolizines, to their use and to pharmaceutical compositions containing them.

GB 2083029B discloses, inter alia, N-methyl or ethyl-N-(1,3,4,6,7,11bα-hexahydro-2H-benzo[a]quinolizin-2β-yl)alkane- and benzenesulphonamides that possess presynaptic (α₂) antagonistic activity in warm blooded animals. The present invention provides certain novel quinolizinyl-bis-sulphonamides.

The novel compounds of the present invention are benzoquinolizines of the general formula (I)

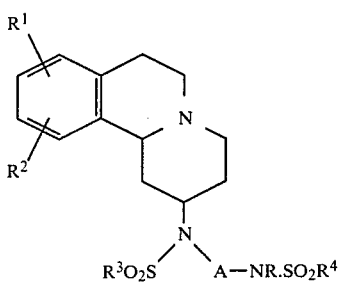

and their pharmaceutically acceptable acid addition salts. In formula (I), R represents hydrogen or lower alkyl, $R^1$ and $R^2$ which may be the same or different each represent hydrogen, lower alkyl, lower alkoxy or halogen, $R^3$ and $R^4$ which may be the same or different each represents lower alkyl, halo(lower)alkyl or aryl and A represents a lower alkylene group having 1 to 3 carbon atoms in the chain between the two N atoms.

The term "lower" as used herein means that the radical referred to contains 1 to 6 carbon atoms. Preferably such radicals contain 1 to 4 carbon atoms. For example, a lower alkyl group may be methyl, ethyl, propyl or butyl. When $R^1$ and/or $R^2$ represent lower alkoxy the group may be, for example, methoxy, ethoxy, propoxy or butoxy. When $R^1$ and/or $R^2$ represents halogen the substituent may be, for example, fluorine, chlorine or bromine. Preferably both $R^1$ and $R^2$ are hydrogen.

The lower alkylene group A may be branched or straight chain provided that there are 1 to 3 carbon atoms in the chain between the two N atoms. For example, the lower alkylene group may be methylene, ethylene, trimethylene or a branched chain group such as ethylethylene or propylene [—CH(CH₃).CH₂—]. Preferably A is ethylene.

When a radical is referred to as "aryl" that radical is preferably a phenyl or substituted phenyl group. The substituted phenyl group can be a phenyl group substituted by one or more substituents chosen from, for example, halogen (e.g. chlorine, fluorine or bromine), alkoxy (e.g. lower alkoxy such as methoxy or ethoxy), lower alkyl (e.g. methyl, ethyl, propyl or butyl), alkylenedioxy (e.g. methylenedioxy or ethylenedioxy), nitro, amino, acylamino (particularly lower acylamino), lower alkylamino, diloweralkylamino or trifluoromethyl.

Examples of $R^3$ and $R^4$ are lower alkyl, such as methyl, ethyl, propyl or butyl, aryl such as phenyl or phenyl substituted by one or more of the substituents mentioned above and halo(lower)alkyl. The halo substituent in a halo(lower)alkyl group may be fluorine, chlorine, bromine or iodine. More than one halo atom may be present in the halo(lower)alkyl group. if more than one halo atom is present the halo atoms may be on the same carbon atom of the (lower)alkyl radical or on different carbon atoms (if the radical contains more than one carbon atom). Examples of halo(lower)alkyl groups include, for example, trifluoromethyl and chloromethyl.

Preferably $R^4$ is lower alkyl, e.g. methyl, and $R^3$ is lower alkyl (e.g. methyl or propyl) or phenyl.

Preferably R is hydrogen.

The compounds of the invention in which $R^3$ and $R^4$ are the same may be prepared by reacting a reactive derivative of a sulphonic acid of formula $R^5SO_2OH$ (II) (where $R^5$ has the meanings of $R^3$ and $R^4$ above) with a benzoquinolizine of the general formula

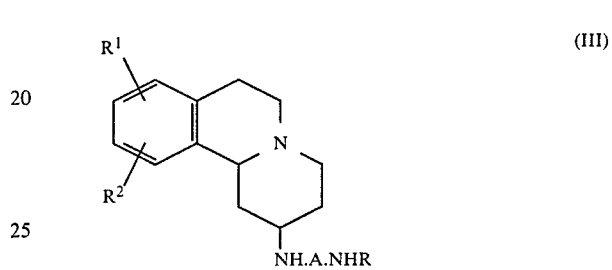

(wherein R, $R^1$, $R^2$ and A are as defined above) and, if required, converting a free base into a pharmaceutically acceptable acid addition salt. The reactive derivative of the sulphonic acid can be, for example, the acid halide or anhydride. Preferably it is the acid halide, i.e. a compound of formula $$R^5SO_2X \qquad (V)$$

(where $R^5$ is as defined above and X is halogen, preferably chlorine). The reaction is generally carried out under basic conditions.

The starting materials of general formula (III) are novel and may be prepared by reductive amination of a ketone of general formula

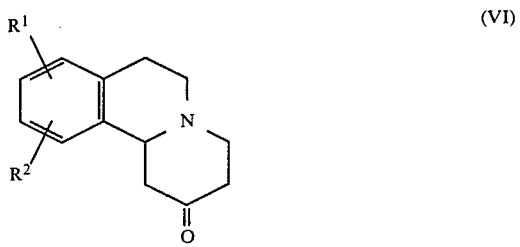

where $R^1$ and $R^2$ have the meanings given above. For example, the ketone may be reacted with a diamine of formula $$NH_2—A—NHR \qquad (VII)$$

(where A and R have the meanings given above) and with a hydride transfer agent, e.g. sodium cyanoborohydride. When R in the diamine is a lower alkyl group it may be necessary to replace the hydrogen on the amino carrying the lower alkyl substituent with a protecting group, such as benzyl and remove the protecting group after the reductive amination.

The starting materials of formula (III) may be prepared by an alternative method comprising reductive amination (by reaction with a diamine of formula VII and e.g. a hydride transfer reagent such as sodium borohydride) or a quaternary salt recursor of the ketone (VI), the quaternary salt having the formula:

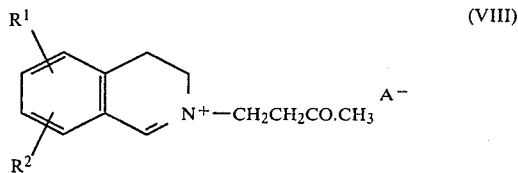
(VIII)

(where $R^1$ and $R^2$ have the meanings given above and $A^-$ is an anion, e.g. halide).

Compounds of the invention in which $R^3$ and $R^4$ are the same or different may be prepared by other alternative methods. For example, a benzoquinolizine of general formula (IX)

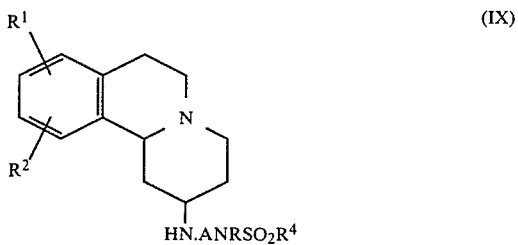
(IX)

(wherein A, R, $R^1$, $R^2$ and $R^4$ have the meanings given above) may be reacted with a reactive derivative of the sulphonic acid of formula (II) above, in an analogous manner to that described above in connection with the reaction of the benzoquinolizine (III). The benzoquinolizine (IX) is novel and may be prepared by known methods. For example the benzoquinolizine of formula (III) may be selectively sulphonated with the reactive derivative of the sulphonic acid (II) using the requisite amount of reactive derivative for forming the monosulphonamide (IX) rather than the disulphonamide (I); it may be necessary to block one of the amine groups in the diamine (III) with a protecting group such as benzyl and remove the protecting group after the sulphonation. The benzoquinolizine (IX) alternatively may be prepared by reductive amination of the ketone (VI) with an amine $NH_2ANRSO_2R^4$ (where A, R and $R^4$ have the meanings given above) and a hydride transfer agent such as sodium borohydride.

Another method of preparing the compounds of the invention comprises reaction of a benzoquinolizine of general formula

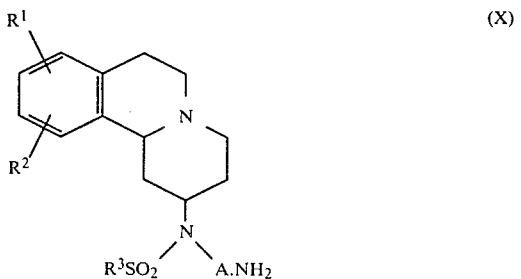
(X)

(where A, $R^1$, $R^2$ and $R^3$ are as defined above) with a reactive derivative of the sulphonic acid of formula (II) in an analogous manner to that described above in connection with the reaction of the benzoquinolizine (III). The benzoquinolizine starting material of formula (X) is novel and may be prepared by methods known per se. For example, a benzoquinolizine of general formula

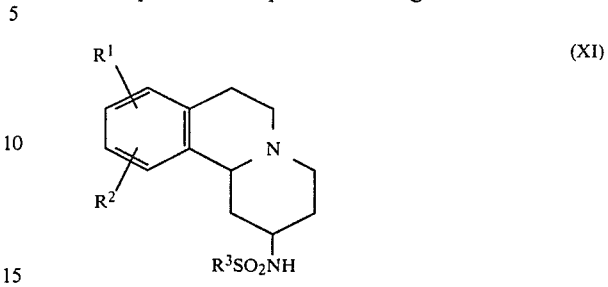
(XI)

(where $R^1$, $R^2$ and $R^3$ have the meanins given above) may be reacted with a phthalimido protected haloamine of formula

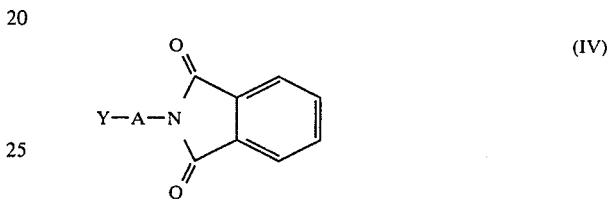
(IV)

(where A has the meaning given above and Y is halogen, preferably bromine) in presence of a strong base such as sodium hydride or lithium diisopropylamide and the phthalimido protecting group removed.

Yet another method of preparing the compounds of the invention comprises reaction of a benzoquinolizine of formula (XI) above with a compound of formula $$X-A-NRSO_2R^4 \qquad (XII)$$

(where X, A and $R^4$ are as defined above) in presence of a strong base such as sodium hydride or lithium diisopropylamide.

Compounds of the invention in which R is lower alkyl may also be produced by alkylation of the compounds of the invention in which R is hydrogen. Compounds of the invention in which $R^3$ and/or $R^4$ is amino substituted phenyl may be prepared by reduction of compounds in which the $R^3$ and/or $R^4$ is nitro substituted phenyl. Similarly compounds in which $R^3$ and/or $R^4$ is acylamino substituted phenyl may be prepared by acylation of compounds in which $R^3$ and/or $R^4$ is amino substituted phenyl.

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compound.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of the invention possess two asymmetric carbon atoms and hence can exist in various stereochemical forms. In addition they can exist as cis or trans isomers. It will be realised that if the starting material of formula (III) is a mixture of isomers the product of formula (I) will also be a mixture of isomers unless the mixture is separated by standard procedures. The preferred compounds of the invention are the trans isomers in which the —N(SO$_2$R$^3$).A.NR.SO$_2$R$^4$ group is in the equatorial position, i.e. compounds of the general formula (XIII)

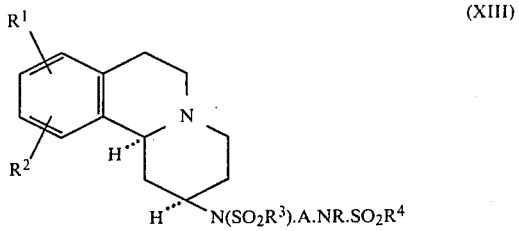

(XIII)

and the pharmaceutically acceptable acid addition salts thereof. These compounds can be prepared by the methods described above from the corresponding trans isomer starting material.

The present invention also provides the novel intermediates of general formulae (III), (IX) and (X). Such compounds have the general formula (XIV)

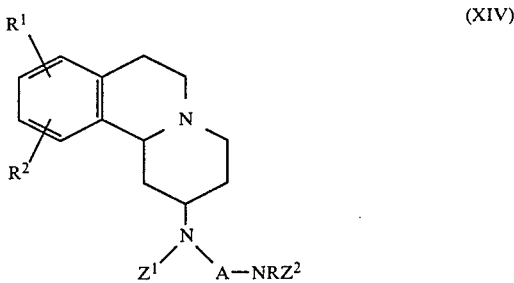

(XIV)

wherein R$^1$, R$^2$ and A are as defined above and Z$^1$ and Z$^2$ are both hydrogen and R is hydrogen or lower alkyl or Z$^1$ is hydrogen, Z$^2$ is SO$_2$R$^4$ (where R$^4$ is as defined above) and R is hydrogen or lower alkyl or Z$^1$ is SO$_2$R$^3$ (where R$^3$ is as defined above), Z$^2$ is hydrogen and R is hydrogen.

The compounds of the present invention possess pharmacological activity. In particular the compounds possess $\alpha_2$-adrenoceptor antagonistic activity in warm blooded animals and hence are of value in conditions where antagonism of the $\alpha_2$-adrenoceptor is desirable, for example, as antidepressants, in treatment of diabetes and in inhibiting blood platelet aggregation.

The compounds of the invention are tested for $\alpha_2$-adrenoceptor antagonistic activity on the rat field stimulated vas deferens preparation using a modification of the metod of Drew, Eur. J. Pharmac., 1977, 42, 123-130. The procedure is described below.

Desheathed vasa deferentia from sexually mature rats were suspended in a 6 ml organ bath in Krebs solution at 37° and bubbled with 5% CO$_2$ in oxygen. Platinum ring electrodes were positioned above and below the tissue for field stimulation, the stimulus parameters being 0.1 Hz 1 ms pulse width at supramaximal voltage. Twitch responses were recorded isotonically with a 0.5 g loading. Clonidine hydrochloride was used as the $\alpha$-adrenoceptor agonist and cumulative concentration-response curves were constructed for the inhibition of twitch obtained with clonidine in the range 0.125 to 4 ng ml$^{-1}$. After washing out clonidine, the twitch response quickly recovered and an antagonist was then introduced into the Krebs reservoir. Clonidine concentration-response curves were repeated 90 min after introduction of the antagonist. The concentration of clonidine producing 50% inhibition of twitch before and after introduction of antagonist were obtained and the dose-ratio for clonidine was calculated. Various concentrations of the antagonists were used.

These results were plotted in the manner described by Arunlakshana & Schild, Br.J.Pharmac. Chemother., 1959, 14, 48-58 and the values of pA$_2$ and slope were calculated. The compounds of the invention possess potent $\alpha_2$-adrenoceptor antagonistic activity. For example, N-[(2$\beta$,11b$\alpha$)-1,3,4,6,7,11b-hexahydro-2H-benzo[a]-quinolizin-2-yl]-N-(2-methanesulphonamidoethyl)methanesulphonamide, N-[(2$\beta$,11b$\alpha$)-1,3,4,6,7,11b-hexahydro-2H-benzo[a]quinolizin-2-yl]-N-(2-methanesulphonamidoethyl)-n-propanesulphonamide and N-[(2$\beta$,11b$\alpha$)-1,3,4,6,7,11b-hexahydro-2H-benzo[a]-quinolizin-2-yl]-N-(2-methanesulphonamidoethyl)benzenesulphonamide, representative compounds of the invention, have been found to have a pA$_2$ for $\alpha_2$-adrenoceptor antagonistic activity of respectively 7.93, 8.29 and 8.12.

The compounds of the invention generally antagonise the $\alpha_2$-adrenoceptors to a much greater extent than the $\alpha_1$-adrenoceptors. The $\alpha_1$ antagonistic activity can be evaluated by a number of different methods. One method involves assessing the activity on the isolated anococcygeus muscle of the rat. The method is based on that of Gillespie, Br.J.Pharmac., 1972, 45, 404-416. In the procedure male rats (250-360 g) are killed by a blow on the head and bled. The two anococcygeus muscles are removed from their position in the midline of the pelvic cavity, where they arise from the upper coccygeal vertebrae. The muscles are suspended in 5 ml organ baths in Krebs solution containing 10$^{31}$ $^4$M ascorbic acid, to prevent drug oxidation. The tissues are gassed with a 95% oxygen, 5% CO$_2$ mixture and maintained at 37°. Longitudinal muscle contractions are recorded using isotonic transducers. Cumulative dose response curves are then obtained to phenylephrine or in some cases methoxamine, both agents being presynaptic alpha adrenoceptor agonists. The concentration range of phenylephrine or methoxamine used is 0.02 to 0.8 $\mu$g.ml$^{-1}$. The agonist is then washed from the bath and the test drug added to the bathing medium at a concentration of 10$^{-6}$M. After 30 min equilibration with the test drug a further agonist dose response curve is obtained. The washing, equilibration and agonists dosing procedures are then repeated using 10$^{-5}$M and 10$^{-4}$M solutions of the test drug. Estimates of the pA$_2$ value for the test drug as an antagonist of phenylephrine or methoxamine were made from the agonist dose-ratios using the method of Arunlakshana & Schild, Br. J.Pharmac.Chemother., 1959, 14, 48-58.

The pA$_2$ values for $\alpha_1$ antagonistic activity for N-[(2$\beta$,11b$\alpha$)-1,3,4,6,7,11b-hexahydro-2H-benzo[a]-quinolizin-2-yl]-N-(2-methanesulphonamidoethyl)methanesulphonamide, N-[(2$\beta$,11b$\alpha$)-1,3,4,6,7,11b-hexahydro-2H-benzo[a]quinolizin-2-yl]-N-(2-methanesulphonamidoethyl)-n-propanesulphonamide and N-[(2$\beta$,11b$\alpha$)-1,3,4,6,7,11b-hexahydro-2H-benzo[a]-quinolizin-2-yl]-N-(2-methanesulphonamidoethyl)benzenesulphonamide have been found to be respectively 5.32, 5.80 and 6.20 and the $\alpha_2/\alpha_1$ selectivity [i.e. antilog of $(\alpha_2pA_2-\alpha_1pA_2)$] for these compounds are respectively 407, 309 and 83. The compounds show great selectivity towards the $\alpha_2$ receptors.

The invention further provides a compound of formula (I) or a pharmaceutically acceptable acid addition salt for use in antagonising $\alpha_2$-adrenoceptors in a mammal.

The invention also provides a pharmaceutical composition comprising a compound of general formula (II) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a phrmaceutically acceptable liquid carrier such as water, an organic solvent, a mixture of both or pharmaceutically acceptable oils or fats. The liquid carrier can contain other suitable pharmaceutical additives such as solibilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additive as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The following Examples illustrate the invention:

EXAMPLE 1

N-[(2$\beta$,11b$\alpha$)-1,3,4,6,7,11b-hexahydro-2H-benzo[a]-quinolizin-2-yl]ethylenediamine A solution of 2-oxo-1,3,4,6,7,11b$\alpha$-hexahydro-2H-benzo[$\alpha$]quinolizine (4 g, 0.02 mol) in ethanol (40 cm$^3$) was acidified with ethanolic HCl. Ethylenediamine (7.2 g, 0.12 mol) and 2-oxo-1,3,4,6,7,11b$\alpha$-hexahydro-2H-benzo[a]quinolizine (4 g, 0.02 mol) were then added to the above solution and the mixture refluxed for 1.5 hour. The solution was then cooled in ice and sodium borohydride (2 g) added with stirring. The mixture was stirred for 4 hours at ambient temperature and then evaporated. The residue was diluted with water and extracted with chloroform. The extracts were dried and evaporated, the residue was dissolved in ethanol (60 cm$^3$) and acidified with ethanolic HCl to precipitate the amine salt (10.5 g), m.p. 225°–30° C.

EXAMPLE 2

N-[(2$\beta$,11b$\alpha$)-1,3,4,6,7,11b-Hexahydro-2H-benzo[a]-quinolizin-2-yl]-N-(2-methanesulphonamidoethyl)methanesulphonamide Methanesulphonyl chloride (0.72 g, 0.49 cm$^3$) was added over 3 min to a stirred mixture of the amine trihydrochloride from Example 1 (1.06 g, 3 mmol), triethylamine (2.44 cm$^3$, 17.5 mmol), and dichloromethane (25 cm$^3$). After stirring a further 1 hour, TLC showed the reaction was only partially complete. A further 0.25 cm$^3$ of methanesulphonyl chloride was added followed after a further 1 hour by the same quantity again. The solution was then washed with sodium bicarbonate solution, the organic phase was separated, dried, and evaporated. The residue was eluted down an alumina column (70 g, Act. I. Woelm) with chloroform to give 0.63 g of pure product. The base was dissolved in ethanol and acidified with ethanolic HCl followed by addition of ether to precipitate the title compound as the hydrochloride hemihydrate 0.65 g, m.p. 152° C.

EXAMPLE 3

N-[(2$\beta$,11b$\alpha$)-1,3,4,6,7,11b-hexahydro-2H-benzo[a]-quinolizin-2-yl]-N'-methylethylenediamine A mixture of 4-(3,4-dihydroisoquinolinium)butane-2-one chloride (4.17 g), N-methylethylenediamine (2.6 g) and ethanol (15 cm$^3$) was heated at reflux for 1.5 hour. The solution was then cooled in ice and sodium borohydride (1 g) added. After stirring overnight the solvent was evaporated, the residue was diluted with water and extracted with chloroform. The extract was dried and evaporated, the residue was dissolved in ethanol and acidified with ethanolic hydrogen chloride to precipitate the title compound as the crystalline trihydrochloride 4.4 g, m.p. 245°–8° C.

EXAMPLE 4

N-[(2β,11bα)-1,3,4,6,7,11b-hexahydro-2H-benzo[a]-quinolizin-2-yl]-N-(2-N'-methylmethanesulphonamido)ethylmethanesulphonamide N-[(2β,11bα)-1,3,4,6,7,11b-hexahydro-2H-benzo[a]-quinolizin-2-yl]-N'-methylethylenediamine trihydrochloride (1.84 g) was basified with sodium hydroxide and extracted into $CH_2Cl_2$. The extract was dried and evaporated. The residue obtained above was dissolved in $CH_2Cl_2$ (20 cm$^3$) and triethylamine (1.5 g) added, followed by dropwise addition of methanesulphonyl chloride (0.7 ml) to the stirred mixture. After stirring for a further 15 min. the solution was washed with aqueous sodium carbonate, dried and evaporated. The residue was crystallised from ethanol (15 ml) to give the title base (1.1 g). The base was suspended in ethanol (15 cm$^3$) and acidified with aqueous hydrobromic acid (60% w/v) to precipitate the title compound as the hydrobromide, which was collected and recrystallised from aqueous ethanol (20% water) to give 1.1 g, m.p. 235°–7° C.

EXAMPLE 5

N-(2-[((2β,11bα)-1,3,4,6,7,11b-Hexahydro-2H-benzo[a]-quinolizin-2-yl)amino]propanesulphonamide Propanesulphonyl chloride (1.57 g, 1.24 cm$^3$) was added dropwise to a vigorously stirred mixture of N-[(2β,11bα)-1,3,4,6,7,11b-hexahydro-2H-benzo[a]quinolizin-2-yl]ethylenediamine trihydrochloride (3.55 g), potassium carbonate (6.9 g), $CH_2CH_2$ (40 cm$^3$) and water (20 cm$^3$). After addition was completed the mixture was stirred for 0.5 hour then the organic phase was separated, dried and evaporated. The residue was dissolved in ethanol (30 cm$^3$) and acidified with concentrated aqueous hydrobromic acid (60%) to precipitate the title compound dihydrobromide (2.3 g), m.p. 190°–92° C.

EXAMPLE 6

N-((2β,11bα)-1,3,4,6,7,11b-Hexahydro-2H-benzo[a]-quinolizin-2-yl)-N-(2-(1-propanesulphonamido)ethyl)-methanesulphonamide Methanesulphonyl chloride (0.75 cm$^3$) was added dropwise to a stirred ice cooled mixture of the dihydrobromide from Example 5 (2.57 g), triethylamine (2.75 g) and $CH_2Cl_2$ (20 cm$^3$). The solution was then washed with aqueous sodium carbonate solution, dried and evaporated. The residue was crystallised from ethanol (15 cm$^3$) to give the pure title base 1.8 g. The base was suspended in hot methanol (20 cm$^3$) and maleic acid (0.51 g) added. On slow cooling the maleate salt of the title compound crystallised and was collected by filtration and washed with methanol and ethanol to give 2.1 g, m.p. 155°–7° C.

EXAMPLE 7

N-(2-[((2β,11bα)-1,3,4,6,7,11b-Hexahydro-2H-benzo[a]-quinolizine-2-yl)amino]ethyl)benzenesulphonamide Benzenesulphonyl chloride (2.58 cm$^3$) was added dropwise to a stirred ice cooled mixture of N-((2β,11bα)-1,3,4,6,7,11b)-1,3,4,6,7,11b-hexahydro-2H-benzo[a]-quinolizin-2-yl)ethylenediamine trihydrochloride (7.08 g), potassium carbonate (11.04 g), $CH_2Cl_2$ (80 cm$^3$) and water (40 cm$^3$). After 0.5 hour the organic phase was separated, dried and evaporated. The residue was dissolved in methanol (40 cm$^3$) and acidified with aqueous hydrobromic acid (60% w/v S.G. 1.7) to precipitate the title compound as the crystalline dihydrobromide (5.4 g). A sample recrystallised from aqueous methanol gave m.p. 245°–7° C.

EXAMPLE 8

N-(2-[N'-((2β,11bα)-1,3,4,6,7,11b-Hexahydro-2H-benzo[a]quinolizin-2-yl)methanesulphonamido]ethyl)benzenesulphonamide Methanesulphonyl chloride (0.687 g, 0.464 cm$^3$) was added dropwise to a stirred ice cooled mixture of the dihydrochloride product from Example 7 (2.23 g), triethylamine (1.75 g) and $CH_2Cl_2$ (20 cm$^3$). After addition was completed stirring was maintained for a further 0.5 hour and the solution then washed with sodium carbonate solution, dried and evaporated. Crystallisation once from ethanol and twice from toluene gave the title compound (1.3 g), m.p. 146°–7° C.

EXAMPLE 9

N-[(2β,11bα)-1,3,4,6,7,11b-Hexahydro-9,10-dimethoxy-2H-benzo[a]quinolizin-2-yl]ethylenediamine 2-Oxo-9,10-dimethoxybenzoquinolizine (7.8 g) in ethanol (30 cm$^3$) was just neutralized by addition of ethanolic-HCl. Ethylenediamine (10 cm$^3$) was then added and the solution refluxed for 2 hours. The solution was then cooled in ice and sodium borohydride (1.5 g) added carefully with stirring. The mixture was then allowed to stir at ambient temperature over night. The solution was evaporated, diluted with water and extracted into chloroform. The extract was dried and evaporated and the residue dissolved in ethanol (50 cm$^3$) and acidified with ethanolic-HCl to precipitate a gum which crystallised when the mixture was warmed briefly. After cooling in ice the title compound was collected as the crystalline trihydrochloride and washed with ethanol to give 7.3 g, m.p, 259°–62° C.

EXAMPLE 10

N-((2β,11bα)-1,3,4,6,7,11b-Hexahydro-9,10-dimethoxy-2H-benzo[a]quinolizin-2-yl)-N-(2-methanesulphonamidoethyl)methanesulphonamide The trihydrochloride from Example 9 (2.07 g) was basified with sodium hydroxide (1 g) in water (10 ml) and extracted in $CHCl_3$. The extract was dried and evaporated. The residue obtained above was dissolved in $CH_2Cl_2$ (20 cm$^3$) and triethylamine (1.5 g). The solution was cooled in ice and methanesulphonyl chloride (1.2 g, 0.81 cm$^3$) added dropwise with stirring. After addition was complete the mixture was allowed to stand for 15 min then washed with aqueous sodium carbonate, dried and evaporated. The residue was purified by trituration twice with hot ethanol to give the title compound hemihydrate (2.1 g), m.p. 185°–7° C.

EXAMPLE 11

N-(2-[((2β,11bα)-1,3,4,6,7,11b-Hexahydro-2H-benzo[a]-quinolizin-2-yl)amino]ethyl)methanesulphonamide Methanesulphonic anhydride (11.3 g) was added portionwise over 2–3 min to a vigorously stirred, ice cooled mixture of N-[(2β,11bα)-1,3,4,6,7,11b-hexahydro-2H-benzo[a]-quinolizin-2-yl]ethylenediamine trihydrochloride (17.7 g), potassium carbonate (27.6 g), CH$_2$Cl$_2$ (200 cm$^3$) and water (100 cm$^3$). After stirring for a further 0.5 hour the mixture was diluted with water, to dissolve MeSO$_3$K, the organic phase was separated and the aqueous phase extracted with chloroform. The combined organic phases were dried and evaporated. The residue was dissolved in ethanol:methanol (1:1, 300 cm$^3$) and acidified with aqueous hydrobromic acid (60% w/v) to precipitate title compound as the dihydrobromide on ice cooling 13.2 g, m.p. 238°–45° C.

EXAMPLE 12

N-((2β,11bα)-1,3,4,6,7,11b-Hexahydro-2H-benzo[a]-quinolizin-2-yl)-N-(2-methanesulphonamidoethyl)-n-propanesulphonamide The dihydrobromide product of Example 11 was basified by addition of sodium hydroxide (0.4 g) in water (10 cm$^3$) and extracted into chloroform. The extract was dried and evaporated. The residue was dissolved in CH$_2$Cl$_2$ (15 cm$^3$) and triethylamine (0.5 g). The solution was stirred and ice-cooled while propanesulphonyl chloride (0.56 cm$^3$) was added dropwise over 1–2 min. After stirring for 0.5 hour at ambient temperature the solution was washed with sodium carbonate solution, dried and evaporated. The residue was chromatographed on alumina (Woelm Act I, 80 g) with chloroform as eluant, to give 0.58 g of pure title base. The base was dissolved in hot ethanol (6 cm$^3$) and acidified with maleic acid (0.165 g) to precipitate the title compound as the maleate on cooling (0.43 g), m.p. 174°–6° C.

EXAMPLE 13

N-((2β,11bα)-1,3,4,6,7,11b-Hexahydro-2H-benzo[a]-quinolizin-2-yl)-N-(2-methanesulphonamidoethyl)benzenesulphonamide The dihydrobromide product of Example 11 was basified with sodium hydroxide (0.4 g) in water (10 cm$^3$) and extracted in chloroform. The extract was dried and evaporated. The residue was dissolved in CH$_2$Cl (15 cm$^3$) and triethylamine (0.5 g). The solution was stirred and ice-cooled while benzenesulphonyl chloride (0.64 cm$^3$) was added dropwise over 1–2 min. After stirring for 0.5 hour at ambient temperature the solution was washed with aqueous sodium carbonate, dried and evaporated. The residue was chromatographed on alumina (Woelm Act I, 80 g) using chloroform as eluant to give 1.18 g of title base. The base was dissolved in ethanol (12 cm$^3$) and acidified with maleic acid (0.311 g) to precipitate the title compound as the maleate, m.p. 197°–8° C.

EXAMPLE 14

N-(2β,11bα)-1,3,4,6,7,11b-Hexahydro-2H-benzo[a]-quinolizin-2-yl]-N-(2-ethanesulphonamidoethyl)ethanesulphonamide Ethanesulphonyl chloride (2.7 g) was added over about 5 min. to a stirred ice cooled mixture of N-((2β,11bα)-1,3,4,6,7,11b-hexahydro-2H-benzo[a]-quinolizin-2-yl)ethylenediamine (10 mmol, prepared from 3.54 g of the trihydrochloride), triethylamine (2.5 ml) and dichloromethane (25 ml). After addition was complete, the reaction was stirred at ambient temperature for 1 hour, washed with sodium carbonate solution, dried and evaporated. The residue was dissolved in ethanol (30 ml) and acidified with maleic acid (1.28 g) to precipitate the title compound as the maleate (3 g). Recrystallization from methanol gave 2.05 g, m.p. 137°–138° C.

EXAMPLE 15

N-[(2β,11bα)-1,3,4,6,7,11b-Hexahydro-2H-benzo[a]-quinolizin-2-yl]-N-(2-methanesulphonamido)ethyl)-ethanesulphonamide Ethanesulphonyl chloride (1.0 ml) was added dropwise to a stirred, ice cooled mixture of N-(2-[((2β,11bα)-1,3,4,6,7,11b-hexahydro-2H-benzo[a]-quinolizin-2-yl)amino]ethyl)methanesulphonamide (5 mmol, prepared from 2.43 g of the dihydrobromide), triethylamine (1.25 g) and dichloromethane (15 ml). After addition was complete the solution was stirred at ambient temperature for 1 hour, washed with sodium carbonate solution, dried and evaporated. The residue was chromatographed on neutral alumina to give title base 1.56 g. The base was dissolved in ethanol (15 ml) and acidified with maleic acid (0.46 g) to precipitate the maleate (1 g). Recrystallization from water (about 7 ml) gave 0.8 g, m.p. 192°–3° C.

EXAMPLE 16

N-[(2β,11bα)-1,3,4,6,7,11b-Hexahydro-2H-benzo[a]-quinolizin-2-yl]-N-(2-chloromethanesulphonamidoethyl)chloromethanesulphonamide Chloromethanesulphonyl chloride (3.12 g) was added over about 5 min. to a stirred, ice cooled mixture of N-((2β,11bα)-1,3,4,6,7,11b-hexahydro-2H-benzo[a]-quinolizin-2-yl)ethylenediamine (10 mmol, prepared from 3.54 g at the trihydrochloride), triethylamine (2.5 g) and dichloromethane (25 ml). After addition was complete, the reaction was stirred for 1 hour at ambient temperature then washed with sodium carbonate solution, dried and evaporated. The residue was chromatographed on neutral alumina using chloroform as eluent to give 1.8 g of title base. The base was dissolved in acetone and acidified with maleic acid (0.5 g, 5% xs) to precipitate the maleate 0.55 g, m.p. 135°–136° C.

EXAMPLE 17

N-[(2β,11bα)-1,3,4,6,7,11b-Hexahydro-2H-benzo[a]-quinolizin-2-yl]-N-(2-methanesulphonamidoethyl)-4-fluorobenzenesulphonamide 4-Fluorobenzenesulphonyl chloride (1.0 g) dissolved in dichloromethane (50 cm$^3$) was added dropwise over 5 min. to a stirred, ice cooled mixture of N-(2-[((2β,11bα)-1,3,4,6,7,11b-hexahydro-2H-benzo[a]-quinolizin-2-yl)amino]ethyl)methanesulphonamide, dihydrobromide (2.0 g) and triethylamine (1.9 cm$^3$) in dichloromethane (50 cm$^3$). The solution was stirred overnight at ambient temperature, washed with aqueous sodium carbonate solution followed by brine. The organic phase was dried (MgSO$_4$) and concentrated in vacuo to yield a brown syrup which was chromatographed (neutral Al$_2$O$_3$, CHCl$_3$). Two major fractions were obtained, concentrated in vacuo, and then both converted to the acid maleate by adding a solution of the base in ethanol to a solution of maleic acid (5% excess) in ethanol. Yields 0.74 g m.p. 182°–4° C. and 0.60 g m.p. 183°–5° C.

EXAMPLE 18

N-[(2β,11bα)-1,3,4,6,7,11b-Hexahydro-2H-benzo[a]-quinolizin-2-yl]-N-(2-methanesulphonamidoethyl)toluene-4-sulphonamide p-Toluenesulphonyl chloride (1.0 g) dissolved in dichloromethane (50 cm$^3$) was added dropwise over 5 min. to a stirred, ice cooled mixture of N-(2-[((2β,11bα)-1,3,4,6,7,11b-hexahydro-2H-benzo[a]quinolizin-2-yl)amino]ethyl)methanesulphonamide, dihydrobromide (2.0 g) and triethylamine (1.9 cm$^3$) in dichloromethane (50 cm$^3$). The solution was stirred overnight at ambient temperature, washed with aqueous sodium carbonate solution followed by brine. The organic phase was dried (MgSO$_4$) and concentrated in vacuo to yield a brown syrup which was chromatographed (neutral Al$_2$O$_3$, CHCl$_3$) and the relevant fractions combined and concentrated in vacuo. The residue was dissolved in ethanol and warmed gently whereupon the title product crystallised. The product was collected by filtration, washed with ethanol and dried in vacuo. Yield 0.70 g, m.p. 150°–4° C.

EXAMPLE 19

N-[(2β,11bα)-1,3,4,6,7,11b-Hexahydro-2H-benzo[a]-quinolizin-2-yl]-N-(2-methanesulphonamidoethyl)-4-methoxybenzenesulphonamide 4-Methoxybenzenesulphonyl chloride (1.1 g) dissolved in dichloromethane (50 cm$^3$) was added dropwise over 5 min. to a stirred, ice cooled mixture of N-(2-[((2β,11bα)-1,3,4,6,7,11b-hexahydro-2H-benzo[a]-quinolizin-2-yl)amino]ethyl)methanesulphonamide, dihydrobromide (2.0 g) and triethylamine (1.9 cm$^3$) in dichloromethane (50 cm$^3$). The solution was stirred overnight at ambient temperature, washed with aqueous sodium carbonate solution followed by brine. The organic phase was dried (MgSO$_4$) and concentrated in vacuo to yield a yellow syrup which was chromatographed (neutral Al$_2$O$_3$, CHCl$_3$) and the relevant fractions combined and concentrated in vacuo. The residue was dissolved in ethanol and warmed gently whereupon the title base crystallised. The product was collected by filtration, washed with ethanol and dried in vacuo. Yield 1.41 g, m.p. 148°–52° C.

EXAMPLE 20

N-[(2β,11bα)-1,3,4,6,7,11b-Hexahydro-2H-benzo[a]-quinolizin-2-yl]-N-(2-methanesulphonamidoethyl)-4-nitrobenzenesulphonamide 4-Nitrobenzenesulphonyl chloride (1 g) was added portionwise over 2–3 min. to a stirred, ice cooled mixture of N-(2-[((2β,11bα)-1,3,4,6,7,11b-hexahydro-2H-benzo[a]-quinolizin-2-yl)amino]ethyl)methanesulphonamide (4 mmol, prepared from 1.94 g of the dihydrobromide), triethylamine (0.5 g) and dichloromethane (15 ml). After addition was complete, the solution was stirred at ambient temperature for 1 hour, washed with sodium carbonate solution, dried and evaporated. The residue was chromatographed, on neutral alumina to give 0.7 g of title compound. Recrystallisation from ethyl acetate gave 0.4 g, m.p. 177°–178° C.

EXAMPLE 21

N-[2β,11bα)-1,3,4,6,7,11b-Hexahydro-2H-benzo[a]-quinolizin-2-yl]propane-1,3-diamine A mixture of 3,4-dihydro-2-(3-oxobutyl)isoquinolinium chloride (38.4 g) and 1,3-propanediamine (67 cm$^3$) was refluxed for 1½ hours in ethanol (100 cm$^3$). The reaction was then cooled in ice and sodium borohydride (8 g) added portionwise with stirring. Stirring was continued overnight at room temperature then the mixture concentrated in vacuo. The residue was carefully hydrolysed with water and then extracted with dichloromethane. The combined organic phases were washed (brine), dried (Na$_2$SO$_4$), and evaporated to dryness. The residue was dissolved in ethanol and acidified with ethanolic hydrogen chloride to precipitate the trihydrochloride (44.5 g).

The salt was converted to the free base and used in the preparation of N-(3-[((2β,11bα)-1,3,4,6,7,11b-hexahydro-2H-benzo[a]-quinolizin-2-yl)amino]propyl)methanesulphonamide.

EXAMPLE 22

N-(3-[((2β,11bα-1,3,4,6,7,11b-Hexahydro-2H-benzo[a]-quinolizin-2-yl)amino]propyl)methanesulphonamide A solution of methanesulphonic anhydride (9.0 g) in dichloromethane (100 cm$^3$) was added dropwise over 2–3 mins. to a rapidly stirred, ice-cooled mixture of N-[(2β,11bα)-1,3,4,6,7,11b-hexahydro-2H-benzo[a]-quinolizin-2-yl]propane-1,3-diamine (10.5 g), potassium carbonate (16.5 g), dichloromethane (100 cm$^3$) and water (100 cm$^3$). The reaction was stirred for a further 0.5 hr. then the organic phase was separated, washed (brine), dried (Na$_2$SO$_4$), and concentrated in vacuo to leave a viscous dark brown syrup (13.6 g).

The residue was dissolved in ethanol (125 cm$^3$) and a solution of oxalic acid dihydrate (10.6 g) in ethanol (75 cm$^3$) was added. The solution was allowed to crystallise overnight then the white crystalline salt collected by filtration, washed well with ethanol and dried in vacuo to yield the dioxalate (16.6 g) which could be recrystallised from methanol/water (1:1).

The salt was converted to the free base and used in the preparation of N-[(2β,11bα)-1,3,4,6,7,11b-hexahydro-2H-benzo[a]-quinolizin-2-yl]-N-(3-methanesulphonamidopropyl)methanesulphonamide.

EXAMPLE 23

N-((2β,11bα)-1,3,4,6,7,11b-Hexahydro-2H-benzo[a]-quinolizin-2-yl)(3-methanesulphonamido-n-propyl)methanesulphonamide A solution of methanesulphonyl chloride (0.71 g) in dichloromethane (20 cm$^3$) was added dropwise to an ice-cooled stirring solution of the product of Example 22 (2.0 g) and triethylamine (0.9 cm$^3$, 0.65 g) in dichloromethane (20 cm$^3$). The reaction was allowed to stir overnight at room temperature then washed with aqueous sodium carbonate solution. The organic phase was dried (MgSO$_4$) and concentrated in vacuo to yield a pale brown syrup. This was dissolved in isopropanol and acidified with ethanolic hydrogen chloride to yield the pure product hydrochloride as a white solid. The material was collected by filtration washed with a little cold IPA and dried in vacuo at about 80° C. Yield 0.74 g.

I claim:

1. A compound selected from the group consisting of a benzoquinolizine of the formula

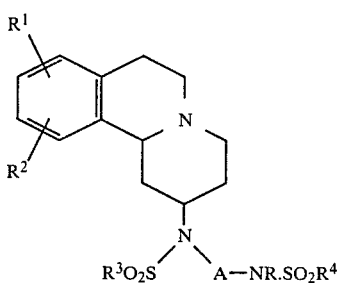

and a pharmaceutically acceptable acid addition salt thereof, wherein R represents hydrogen or lower alkyl, $R^1$ and $R^2$ which may be the same or different each represent hydrogen, lower alkyl, lower alkoxy or halogen, $R^3$ and $R^4$ which may be the same or different each represents lower alkyl, halo(lower)alkyl or aryl and A represents a lower alkylene group having 1 to 3 carbon atoms in the chain between the two N atoms.

2. A compound as claimed in claim 1 wherein A is ethylene.

3. A compound according to claim 1 which is N-[(2β,11bα)-1,3,4,6,7,11b-hexahydro-2H-benzo[a]-quinolizin-2-yl]-N-(2-methanesulphonamidoethyl)methanesulphonamide or a pharmaceutically acceptable salt thereof.

4. A compound according to claim 1 which is N-((2β,11bα)-1,3,4,6,7,11b-hexahydro-2H-benzo[a]-quinolizin-2-yl)-N-(2-methanesulphonamidoethyl)-n-propanesulphonamide or a pharmaceutically acceptable salt thereof.

5. A compound according to claim 1 which is N-((2β,11bα)-1,3,4,6,7,11b-hexahydro-2H-benzo[a]-quinolizin-2-yl)-N-(2-methanesulphonamidoethyl)benzenesulphonamide or a pharmaceutically acceptable salt thereof.

6. A compound according to claim 1 which is N-[(2β,11bα)-1,3,4,6,7,11b-hexahydro-2H-benzo[a]-quinolizin-2-yl]-N-(2-N'-methylmethanesulphonamido)ethylmethanesulphonamide, N-((2β, 11bα)-1,3,4,6,7,11b-hexahydro-2H-benzo[a]-quinolizin-2-yl)-N-(2-(1-propanesulphonamido)ethyl)methanesulphonamide, N-(2-[N'-((2β,11bα)-1,3,4,6,7,11b-hexahydro-2H-benzo[a]-quinolizin-2-yl)methanesulphonamido)ethyl]benzenesulphonamide, N-((2β,11bα)-1,3,4,6,7,11b-hexahydro-9,10-dimethoxy-2H-benzo[a]-quinolizin-2-yl)-N-(2-methanesulphonamidoethyl)methanesulphonamide, N-[(2β,11bα)-1,3,4,6,7,11b-hexahydro-2H-benzo[a]-quinolizin-2-yl]-N-(2-chloromethanesulphonamidoethyl)-chloromethanesulphonamide or N-((2β,11bα)-1,3,4,6,7,11b-hexahydro-2H-benzo[a]-quinolizin-2-yl)(3-methanesulphonamido-n-propyl)methanesulphonamide or a pharmaceutically acceptable acid addition salt thereof.

7. A pharmaceutical composition having $α_2$-adrenoceptor antagonistic activity comprising an amount effective to antagonise $α_2$-adrenoceptors of a compound selected from the group consisting of a benzoquinolizine of the formula

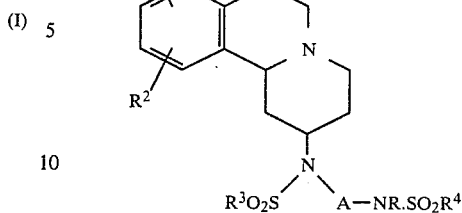

and a pharmaceutically acceptable acid addition salt thereof, wherein R represents hydrogen or lower alkyl, $R^1$ and $R^2$ which may be the same or different each represent hydrogen, lower alkyl, lower alkoxy or halogen, $R^3$ and $R^4$ which may be the same or different each represents lower alkyl, halo(lower)alkyl or aryl and A represents a lower alkylene group having 1 to 3 carbon atoms in the chain between the two N atoms, in association with a pharmaceutically acceptable carrier.

8. A method of antagonising $α_2$-adrenoceptors in warm blooded animals which comprises administering to the animal an effective amount of a compound selected from the group consisting of a benzoquinolizine of the formula

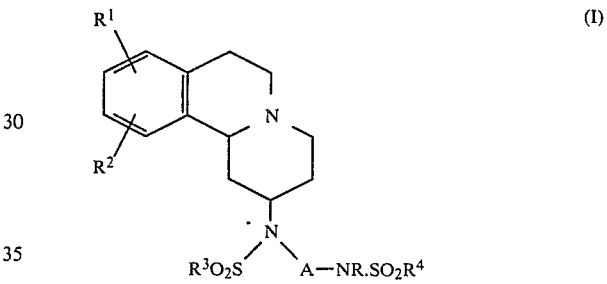

and a pharmaceutically acceptable acid addition salt thereof, wherein R represents hydrogen or lower alkyl, $R^1$ and $R^2$ which may be the same or different each represent hydrogen, lower alkyl, lower alkoxy or halogen, $R^3$ and $R^4$ which may be the same or different each represents lower alkyl, halo(lower)alkyl or aryl and A represents a lower alkylene group having 1 to 3 carbon atoms in the chain between the two N atoms.

9. A compound of the formula

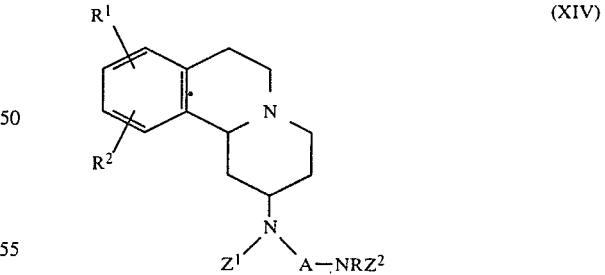

wherein $R^1$, $R^2$ and A are as defined in claim 1 and $Z^1$ and $Z^2$ are both hydrogen and R is hydrogen or lower alkyl or $Z^1$ is hydrogen, $Z^2$ is $SO_2R^4$ (where $R^4$ is as defined in claim 1) and R is hydrogen or lower alkyl or $Z^1$ is $SO_2R^3$ (where $R^3$ is as defined in claim 1), $Z^2$ is hydrogen and R is hydrogen.

10. A compound according to claim 1 which is N-[(2β, 11bα)-1,3,4,6,7,11b-hexahydro-2H-benzo[a]-quinolizin-2yl]-N-(2-ethanesulphonamidoethyl)-ethanesulphonamide or N-[(2β,11bα)-1,3,4,6,7,11b-hexahydro-2H-benzo[a]quinolizin-2-yl]-N-(2-methanesulphonamidoethyl)-ethanesulphonamide or a pharmaceutically acceptable salt thereof.

* * * * *